United States Patent
Stoltz

(10) Patent No.: US 7,717,862 B2
(45) Date of Patent: May 18, 2010

(54) SAMPLING DEVICE AND METHOD FOR OBTAINING SAMPLES OF INTERNAL BODY SUBSTANCES AND METHOD FOR PRODUCING A SAMPLING DEVICE

(75) Inventor: Klas Stoltz, Saltsjobaden (SE)

(73) Assignee: Fargklamman AB, Huddinge (SE)

( * ) Notice: Subject to any disclaimer, the term of this patent is extended or adjusted under 35 U.S.C. 154(b) by 13 days.

(21) Appl. No.: 11/723,479

(22) Filed: Mar. 20, 2007

(65) Prior Publication Data

US 2007/0173738 A1 Jul. 26, 2007

Related U.S. Application Data

(62) Division of application No. 10/697,943, filed as application No. PCT/SE02/00951 on May 17, 2002, now Pat. No. 7,449,001.

(60) Provisional application No. 60/301,254, filed on Jun. 28, 2001.

(30) Foreign Application Priority Data

May 17, 2001 (SE) ..................... 0101738

(51) Int. Cl.
*A61B 5/00* (2006.01)
*A61B 10/00* (2006.01)
*B65D 81/00* (2006.01)
*A61F 2/02* (2006.01)

(52) U.S. Cl. ............. 600/582; 600/562; 600/565; 600/578; 600/300

(58) Field of Classification Search ........ 600/582, 600/562, 565, 578, 300
See application file for complete search history.

(56) References Cited

U.S. PATENT DOCUMENTS

| | | | |
|---|---|---|---|
| 4,239,040 A | | 12/1980 | Hosoya et al. |
| 4,257,427 A | * | 3/1981 | Bucalo ............... 600/582 |
| 4,481,952 A | | 11/1984 | Pawelec |
| 5,170,801 A | * | 12/1992 | Casper et al. .......... 600/582 |
| 5,279,607 A | * | 1/1994 | Schentag et al. ....... 604/890.1 |
| 5,295,266 A | * | 3/1994 | Hinsley et al. ......... 718/101 |
| 5,318,557 A | * | 6/1994 | Gross ................. 604/891.1 |
| 5,971,942 A | | 10/1999 | Gu et al. |

FOREIGN PATENT DOCUMENTS

| | | |
|---|---|---|
| EP | 0 460 327 A1 | 12/1991 |
| EP | 0 662 304 A1 | 7/1995 |

* cited by examiner

*Primary Examiner*—Max Hindenburg
*Assistant Examiner*—Jeffrey G Hoekstra
(74) *Attorney, Agent, or Firm*—Browdy and Neimark, PLLC

(57) ABSTRACT

A sampling device for obtaining samples of internal body substances in the digestive system is a swallowable capsule which allows a sample of the body substance to enter the capsule through an inlet which opens in the digestive tract following contact with the substance to be collected. The capsule inlet initially is sealed and, after the capsule has been swallowed, the inlet opens following contact with the body substance. An inner chamber preserves a vacuum or substantial under pressure when the inlet is sealed by a blocking member adjacent to the inlet. The blocking member is elastic and has a flow permitting configuration which admits the body substance into the inner chamber and a flow preventing configuration which blocks the inlet from the inside of the chamber when the pressure difference has been equalized.

5 Claims, 4 Drawing Sheets

Figure 1:
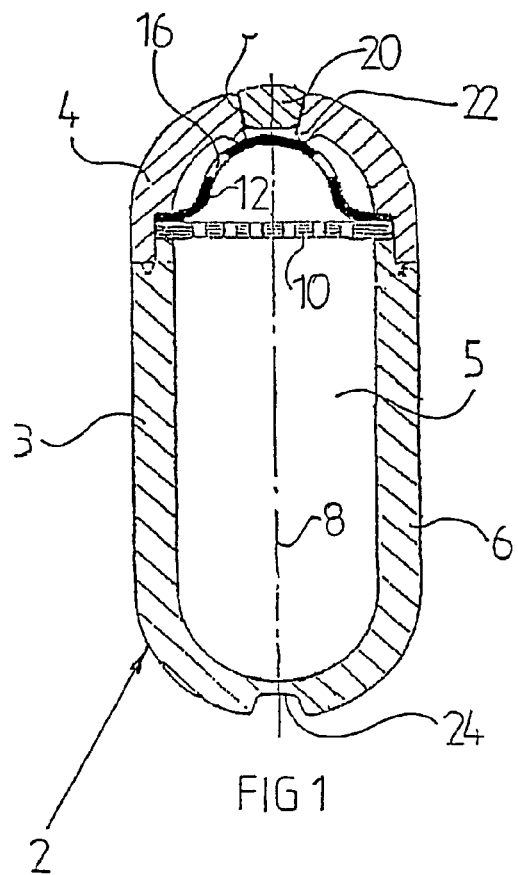

SAMPLING DEVICE AND METHOD FOR OBTAINING SAMPLES OF INTERNAL BODY SUBSTANCES AND METHOD FOR PRODUCING A SAMPLING DEVICE

FIELD OF THE INVENTION

The present invention relates to a sampling device for obtaining samples of internal body substances in the digestive system of humans or animals. The sampling device has the shape of a swallowable capsule which allows a sample of the body substance to enter the capsule through an inlet opening which is opened in a predetermined position of the digestive tract following contact with the body substance to be collected. The invention also relates to a sampling method for obtaining samples of internal body substances and a method for producing the sampling device.

BACKGROUND OF THE INVENTION

Examination of internal body substances, gases or solid particles in the digestive system or the gastrointestinal tract in the human or animal body provides essential medical information for diagnosing and treatment. Examination of a sample of the gastric fluid of a patient provides important information of pH, acid contents, abdominal enzyme activity as well as information for diagnosing gastric ulcer and gastritis, cancer and tumour diseases, etc. A gastroscopic examination gives the physician who is treating a patient important information and plays a great role for a diagnosis. These intubation examinations are thus used extensively. A gastroscopic examination, in which a tube, having a diameter of a little finger, is inserted into the patient's mouth or nose, through the esophagus and to the gastrointestinal system, is difficult to perform and demands the assistance of a physician. For the patient, the intubation of the digestive tract using these methods is a very unpleasant intervention, both physically and psychologically, especially during the insertion of the tube and also when it is pulled out. The intubation demands that the patient is given a local anaesthetic and in some instances even tranquilliser or a general anaesthetic to overcome the stress to which the patient is subjected. The intubation examination methods described above are disadvantageous since they are very time-consuming for a qualified physician and thus expensive and a very unpleasant intervention for the patient.

The application of a swallowable capsule for automatically obtaining samples of internal gastric fluids has been proposed as an alternative examination method and is described in U.S. Pat. No. 4,481,952. The capsule is equipped with mechanisms, which control the opening and closing of the capsule. The mechanisms are blocked by blocking mechanisms, including a mass which is dissolved after a short time following contact with the gastric fluid. The opening of the capsule, the collection of the sample and the reclosing of the capsule takes place automatically in the patient's stomach. The described sampling device is advantageous in many ways. However, it has proved to function unsatisfactorily and has therefore not been widely used. The described capsule is expensive, is mechanically complicated and comprises mutually movable parts, mostly metal parts. As a consequence, the parts tend to jam, fluids tend to leak between the parts, friction forces between the parts must be overcome, e.g. by spring forces, and metal parts, such as springs, may loosen in the gastrointestinal tract causing injuries to the patients.

BASIC IDEA OF THE INVENTION

The object of the present invention is to solve the above-mentioned problems of the prior art by providing a sampling device which operates automatically in the system of a patient and which is simple, inexpensive to produce, reliable and easy to use.

This object is achieved in accordance with the invention in a sampling device and a method for obtaining samples and a method for producing a sampling device as described above and with the characterising features as defined in the attached claims.

In accordance with the invention, a sampling device for automatically obtaining samples of internal body substances is shaped as a capsule such that it may be swallowed by the patient without any stress or pain. In a predetermined position in the digestive system, the capsule is opened and a sample of the body substance is aspirated through an inlet opening into the capsule by the force of a vacuum or substantial underpressure in the capsule. When a predetermined volume of the sampling substance has been collected in the capsule, i.e. the capsule is filled, the inlet opening is automatically closed, sealing it from the inside of the capsule, such that the sample remains in the capsule. The capsule with the collected sample is fed through the gastrointestinal tract of the digestive system and, still with no stress or pain for the patient, out of the human body together with the feces in a normal manner. The capsule with the collected sample subsequently is sent or handed over to a medical institution or laboratory, where the sample is evacuated from the capsule to be analysed.

The sampling device according to the invention is simple and is made of a few essential parts. Just one of these part, the elastic blocking member, is resiliently movable between a flow permitting configuration and a flow preventing configuration and is affected by forces ensuing from the pressure difference between the outside and the inside of the capsule. Through this constructional feature of the closing member, a reliable, simple and inexpensive sampling device is achieved with no metal or mutually movable parts that may jam, leak or come loose in the system and cause injuries to the patient. Through the production method according to the invention a vacuum or substantial underpressure is created in the capsule and this vacuum or substantial underpressure exerts sufficient forces for opening the closing member and for aspiration of a sample of a body substance into the capsule. Through the sampling method according to the invention, the collection of internal body substances can be performed extremely simple and inexpensive and the examination may be carried out without any pain, stress or discomfort to the patient.

SHORT DESCRIPTION OF THE DRAWINGS

Figure 2:
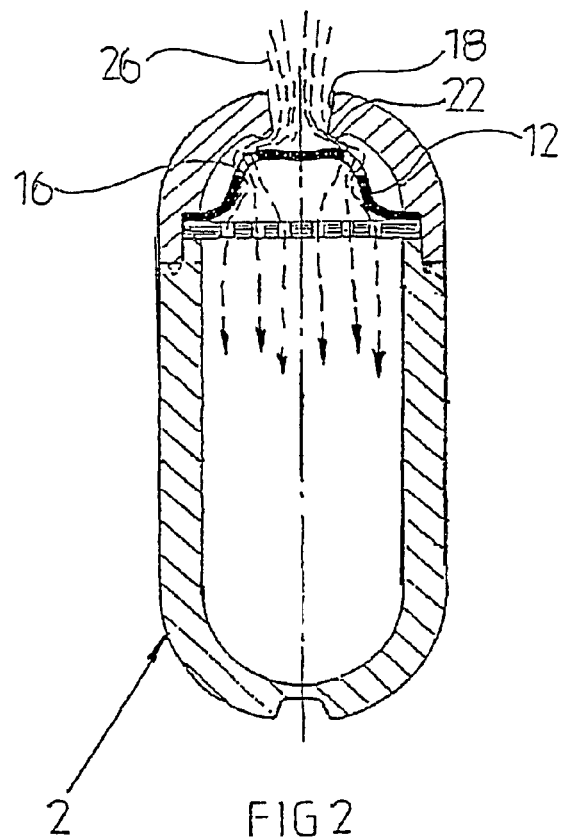
Figure 3:
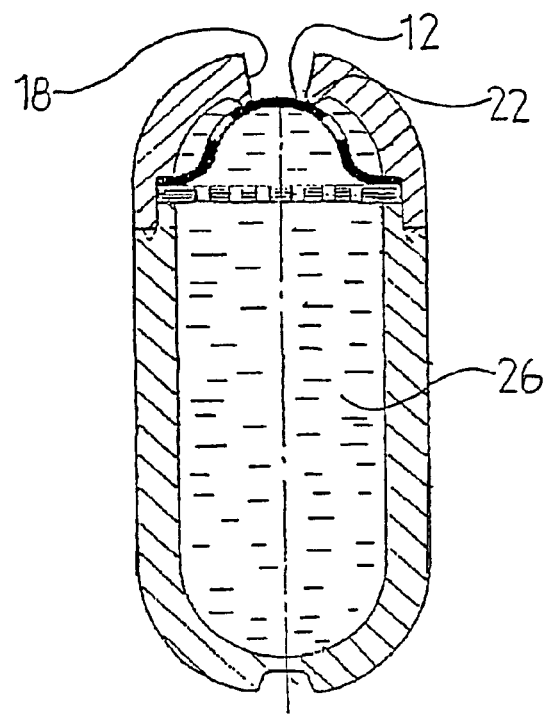
Figure 4:
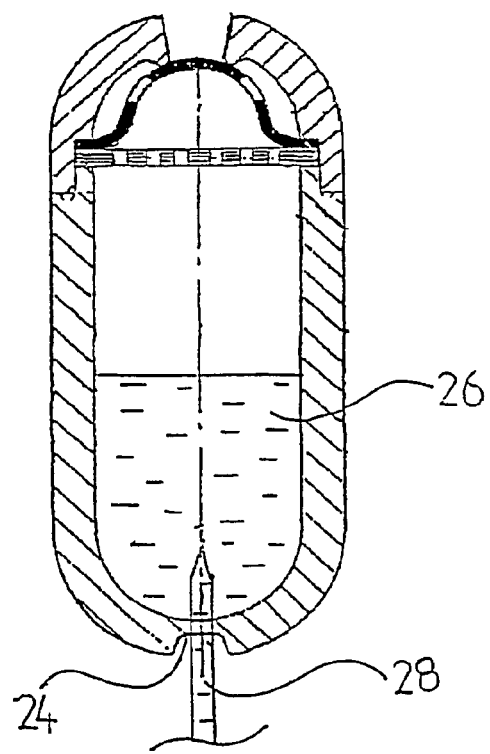
Figure 5:
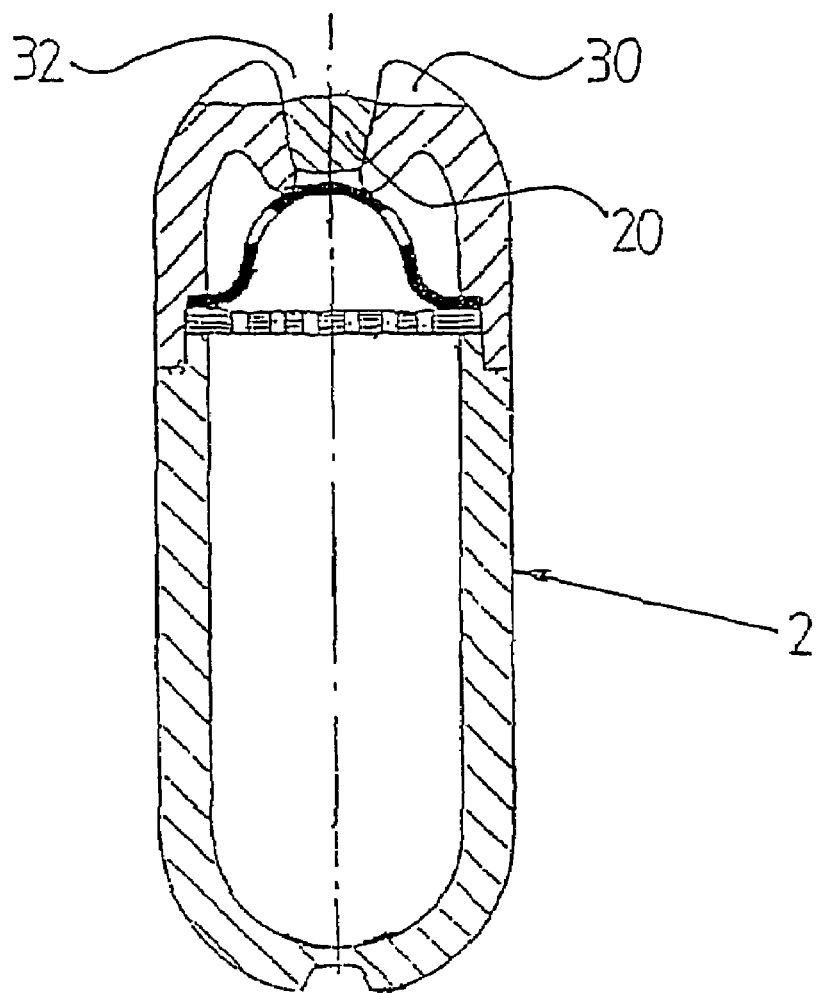
Figure 6:
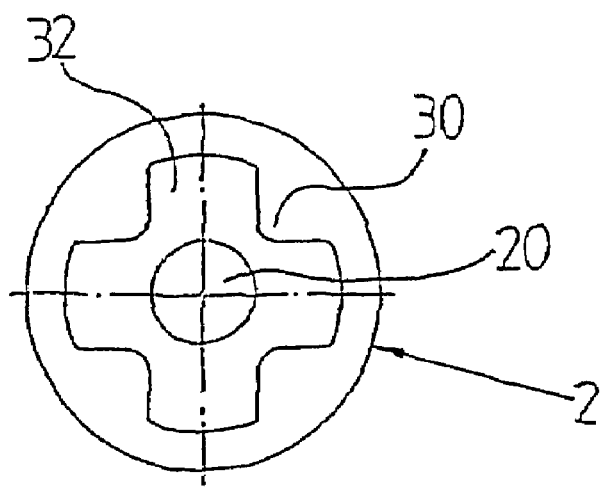
Figure 7:
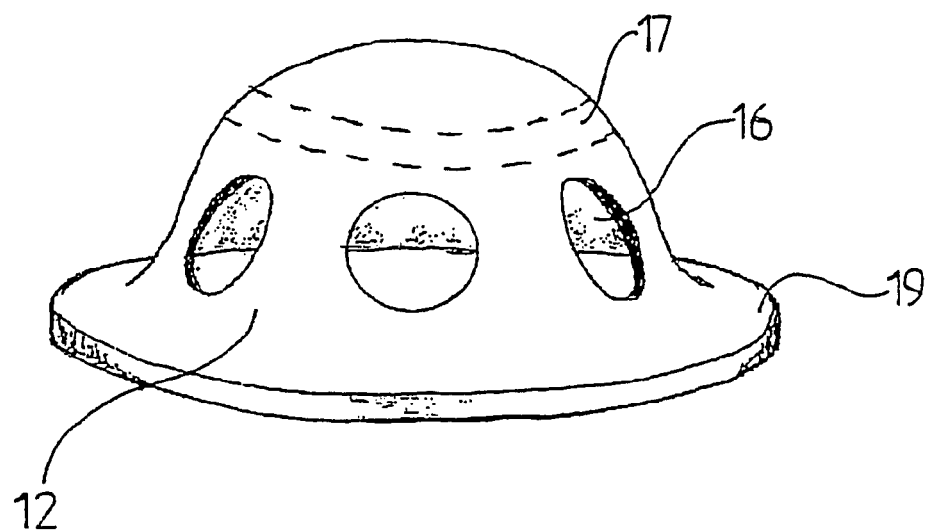
Figure 8:
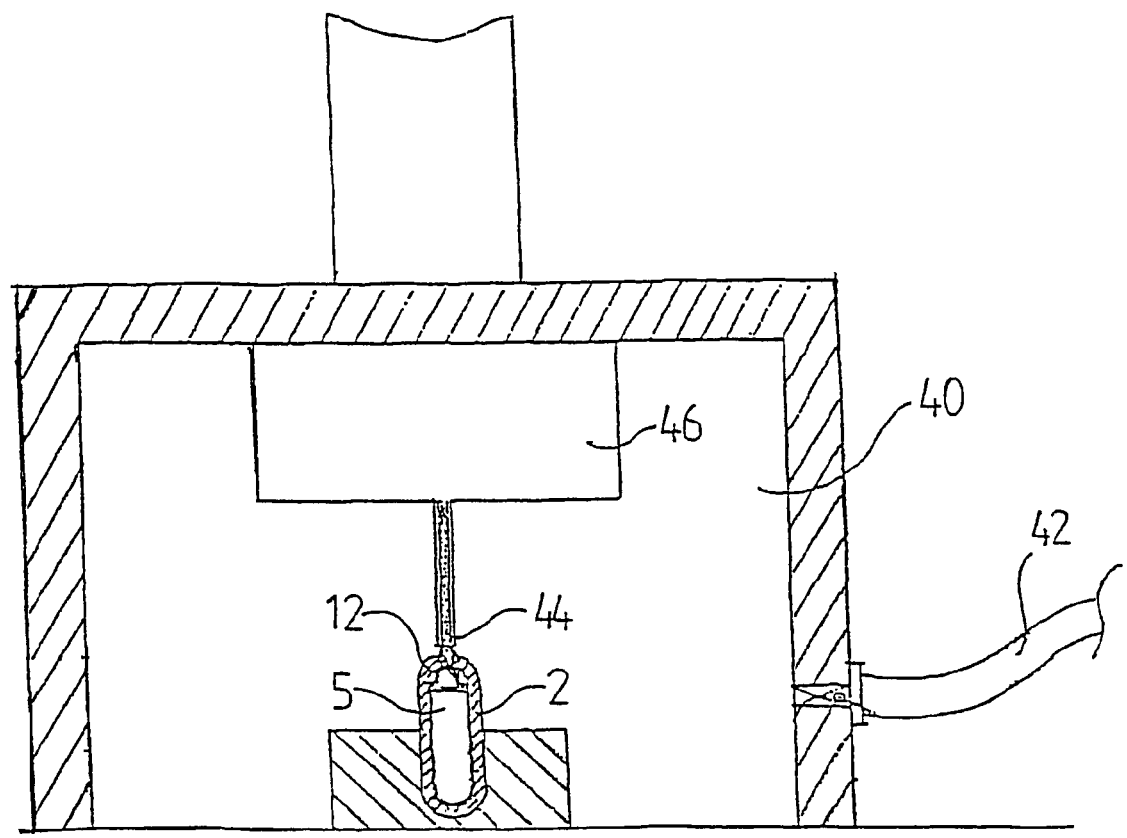

The invention will be described more in detail below with reference to the attached drawings, in which:

FIG. 1 is a sectional view of a sampling device according to a first embodiment of the invention, in a first closed and sealed state, FIG. 2 shows the sampling device of FIG. 1 in a second, open state, and in a flow permitting configuration with the body substance flowing into the device, FIG. 3 shows the sampling device of FIG. 1 in a third, reclosed state, and in a flow preventing configuration in which the body substance has filled up the sampling device, FIG. 4 shows the sampling device of FIG. 1 in a fourth, evacuating state, in which the sample of body substance is evacuated from the capsule to be analysed, FIG. 5 is a sectional view of a sampling device according to a second embodiment of the invention, in a first closed and sealed state, FIG. 6 shows the sampling device of FIG. 5 from above, FIG. 7 shows an enlarged scale perspective view of an embodiment of the blocking member, and FIG. 8 shows a schematic elevation view of the vacuum chamber.

DETAILED DESCRIPTION OF EMBODIMENTS OF THE INVENTION

FIG. 1 is a sectional view of a sampling device according to the invention, said device being designed to obtain samples of internal body substances, such as body fluids, in the digestive tract of a patient. In FIG. 1, the sampling device is shown in a first closed and sealed state, in which it is handed over to be swallowed by a patient, from whom a sample of an internal body fluid, such as the gastric fluid in the stomach, for example, shall be collected.

The sampling device has the shape of a capsule 2, such as a conventional pharmaceutical capsule, and is thus suitable for ingestion. The capsule 2 is preferably elongated and has rounded end portions and preferably a circular or oval-shaped cross-section. The capsule 2 comprises an inner chamber 5 defined by a capsule wall 3.

The capsule 2, preferably made of a thermoplastic material or any other suitable material, is made of at least two capsule members, a cap member 4 and a body member 6, said cap 4 and body 6 members being permanently joined to each other, as will be described more in detail below. The inner chamber 5 of the capsule 2 may comprise a filter 10, preferably clamped in the capsule 2 between the cap member 4 and the body member 6, to filtrate the body fluid sample, when required.

A blocking member 12 in the capsule is shown in an enlarged view in FIG. 7. The inner blocking member 12, such as a membrane valve, made of a flexible, elastic and resilient rubbery material, has a circular fixation edge 19 which is clamped in the capsule 2 between the cap member 4 and the body member 6. In the embodiment as shown, the blocking member 12 has the form of a bulb and has at least one, preferably several, apertures 16 arranged in the slanted side of the bulb. In the closed and sealed state, as shown in FIG. 1, the blocking member 12 bears on a preferably circular contact surface 22 on the inside of the capsule wall 3. The contact or sealing area 17 on the blocking member 12 is shown between the dashed lines in FIG. 7. Through the shape of the blocking member and the resilience of the material, the blocking member 12 bears on the contact surface 22 with a bearing pressure.

The circular contact surface 22, formed as a bulge-formed lining, is arranged on the inside of the capsule wall 3 and extends around an inlet opening 18 in said wall. In the closed and sealed state of the capsule as shown in FIG. 1, the inlet opening 18 is sealed by a plug 20. The plug 20 in the capsule 2 is made of a material which is chosen depending on the application of the capsule, i.e. the specific body fluid to be collected. The plug 20 is dissolved after a short period of time in the body fluid in question, in the embodiment as described, the digestive fluid. Thus, the material of the plug 20 is adapted to the specific fluid or substance in the external environment of the capsule in the position in the body system where the sample is collected. The material of the plug 20 is, for example, gelatine, molten sugar, salt, glue, organic edible materials or any other suitable material. Alternatively, the plug 20 can be made of two or more layers of different materials, which dissolve gradually upon contact with different substances in the external environment of the capsule 2 during its passage through the digestive system. The innermost layer dissolves upon contact with body fluid to be collected by the capsule 2.

A section of the capsule wall 3, preferably in the body member 6 of the capsule, is thinner and forms a notch 24. The notch 24 is used when the body fluid sample in the inner chamber 5 shall be evacuated from the capsule, as will be described more in detail with reference to FIG. 4.

In the inner chamber 5 of the capsule, defined by the capsule wall 3 and the plug 20, a vacuum or substantial underpressure prevails as long as the capsule 2 is in the closed and sealed state as shown in FIG. 1.

When an examination of a body fluid in the digestive system is required, the patient swallows the capsule 2, e.g. the capsule as shown in FIG. 1, without any stress or pain. The size of the capsule 2 may vary depending on the volume of body fluid required for the examination and analysis. A suitable size of a capsule which is easy to swallow has, for example, a length of about 25 mm and a width of about 10 mm.

In FIG. 2, the inlet opening 18 of the capsule 2 has been opened. When the capsule is in the state as shown in FIG. 2, the capsule has previously been swallowed by the patient, has passed the esophagus and has entered into the stomach. During the passage of the capsule 2 from the mouth to the position in the system of the patient in which the sample shall be collected, the patient feels no more discomfort than he feels when he swallows an ordinary pharmaceutical capsule, i.e. a discomfort which is principally non-existing.

When the plug 20 has been dissolved, as shown in FIG. 2, the inlet opening 18 is open. A suction effect is generated by the pressure difference between the external environment of the capsule 2 and the inner chamber 5 in which a vacuum or substantial underpressure prevails. This suction effect forces the resilient blocking member 12 into a flow permitting configuration, as shown in FIG. 2. The body fluid 26 in the external environment of the capsule flows into the inlet opening 18 and exerts a pressure on the resilient and elastic, self-sealing blocking member 12, such that a fluid passage into the chamber 5 is opened between the contact surface 22 and the blocking member 12. The body fluid 26 flows further through the apertures 16 in the blocking member 12, through the filter 10, if any, and into the inner chamber 5, as shown in FIG. 2.

The blocking member 12 is opened and is kept open by the pressure difference between the external environment of the capsule and the inner chamber of the capsule 2. As soon as the external and internal pressure of the capsule have been equalised and the body fluid 26 has filled up the inner chamber 5 of the capsule, the blocking member 12 reverts to a flow preventing configuration, such that the inlet opening 18 is closed and thus the flow of body fluid from the inner chamber 5 of the capsule is prevented. This reclosed state of the capsule is shown in FIG. 3. Since the body fluid sample fills up the inner chamber 5 of the capsule and the fluid is prevented by the blocking member 12 to leave the chamber, the exact volume of the collected body fluid in a sampling capsule can be predetermined. The capsule 2 with the enclosed sample of body fluid 26 is now fed through the gastrointestinal tract and is recovered from the feces of the patient.

FIG. 4 shows the recovered capsule 2 in a state in which the body fluid sample is evacuated from the inner chamber 5 of the capsule. An evacuation needle 28, directly or indirectly connected to an instrument for examination and analysis of the body fluid sample, penetrates the notch 24 of the chamber wall 3 and empties the inner chamber 5.

FIGS. 5 and 6 show a second preferred embodiment of the invention, which differs from the embodiment of FIGS. 1-4 only in that the inlet of the capsule 2 is designed differently. Several, e.g. four in the shown embodiment, protrusions 30 are disposed externally on the capsule 2 at the inlet opening 18. Between the protrusions 30 laterally directed inlet grooves 32 are formed. The protrusions 30 protect the inlet opening 18 in such a way that they prevent the capsule 2 from being adhered to the walls of the digestive system by the suction forces generated by the internal underpressure. A free flow of body fluid through the inlet grooves 32 into the capsule 2 is thus always secured.

As described above, the capsule 2 consists of two members 4, 6 which are permanently joined together. The members 4, 6 are preferably made of injection-moulded thermoplastic, such as Macrolon® D for example, which is a strong, acid resistant and transparent material and thus suitable for this purpose.

The blocking member 12 is preferably made of an elastic rubbery material and may be injection-moulded. The shape (see for example FIGS. 3-5) and the material properties of the blocking member 12 generate the self-closing function and force the blocking member to bear on and seal off the inlet opening 18 from the inside of the capsule 2.

The sampling device according to the invention is made of a few parts, i.e. the cap member 4 with the plug 20, the body member 6, the blocking member 12 and, when required, also the filter 10. As shown in FIG. 7, these parts are fully or partly assembled in a vacuum chamber 40, in which a vacuum or substantial underpressure is maintained by means of a vacuum pump (not shown) connected to the vacuum chamber through the vacuum hose 42. In accordance with the invention, at least the assembly-step that finally seals off the inner chamber 5 of the capsule from the external environment shall be carried out in the vacuum chamber 40 in order to achieve a vacuum or substantial underpressure in the inner chamber 5, such that sufficient suction forces are generated to force the blocking member 12 to a flow permitting configuration and the body fluid sample to enter and fill the capsule.

To assemble the sampling device according to the invention, the blocking member 12 and possibly the filter 10 are initially mounted in the cap member 4 or the body member 6 and subsequently the two members of the capsule are permanently joined together, preferably by ultrasonic welding. The plug 20 may previously have been inserted in the inlet opening 18 of the capsule. In that case, the joining of the two members 4, 6 together, constitutes the assembly-step that seals off the inner chamber 5 of the capsule. Thus, at least this assembly-step must be carried out in the vacuum chamber 40.

Alternatively, when the blocking member 12 and the filter 10 have been mounted in either of the two members 4, 6 of the capsule 2, these two members 4, 6 are permanently joined together, and then the final sealing of the inner chamber 5 of the capsule is made by introducing the plug 20 into the inlet opening 18. Thus, at least this final assembly-step shall be carried out in the vacuum chamber 40. The plug 20, for example made of an organic glue, is quickly set when it is cooled. In the embodiment as shown in FIG. 7, the plug 20 is applied by means of a nozzle 44 and the glue is fed into the nozzle from the container 46. In the embodiment of FIG. 7, the nozzle 44 initially is inserted into and through the inlet opening 18 of the capsule in the vacuum chamber, such that the elastic and self-closing blocking member 12 is forced by the nozzle 44 to open the communication to the inner chamber 5 of the capsule and the vacuum in the vacuum chamber is transmitted to the inner chamber 5. The nozzle 44 is then withdrawn to the position of the inlet opening 18, where the plug 20 is applied by the nozzle 44 and sets, such that the capsule with its internal vacuum or substantial underpressure is finally sealed. Thus, in this assembly-step, the nozzle 44 is first used to open the blocking member 12 and subsequently to apply the plug 20 of glue in the inlet opening 18.

The capsule 2 may further be provided with an additional outer, covering film of gelatine or any other suitable material, which is dissolved in the digestive system. The film may be applied in order to minimise the resistance when the capsule is swallowed by the patient.

It will be understood that the invention is not restricted to the aforedescribed exemplifying embodiments thereof and that several conceivable modifications of the invention are possible within the scope of the following claims. For example, the plug may be formed to be fully dissolved after a predetermined time in the digestive system, such that a time delay of the opening of the inlet opening is obtained. The elastic blocking member may have other forms and shapes and be placed differently in the capsule. Instead of one single inlet opening, as described in the embodiments above, several adjoining inlet openings may be provided in the capsule. In the description above, only samples of body fluids have been discussed. It should, however, be noted that the sampling device according to the invention also may be used to collect samples comprising gases and/or solid particles in the digestive system.

What is claimed is:

1. A sampling method for obtaining samples of internal body substances in a digestive tract of a patient, wherein an elongated capsule (2) having rounded end-portions is swallowed by the patient and the capsule (2) is opened in a predetermined position of the digestive tract following contact with a body substance to be collected, the method comprising:

a) opening an inlet opening (18) provided in an end-portion of the capsule (2) and having the inlet opening extending in a direction along a longitudinal axis of the elongated capsule to initiate collection of a sample of the body substance by dissolving a plug member (20) within the inlet opening (18) in the capsule wall (3) following contact with the body substance to be collected;

b) opening a flexible, self-sealing blocking member (12) comprised of a singular body, disposed inside the capsule (2), by flexible movement of the blocking member (12) in the direction along the longitudinal axis of the elongated capsule to collect the sample of the body fluid by the force of vacuum or substantial under-pressure in the capsule (2) when the plug member (20) has been dissolved; and c) blocking the inlet opening (18) with the flexible blocking member (12) by flexible movement of the flexible blocking member in the direction along the longitudinal axis of the elongated capsule, caused by internal resilience of the blocking member from the inside of the capsule (2) when the vacuum or substantial under-pressure in the capsule has been equalised.

2. The method of claim 1 wherein the plug member (20) comprises two or more layers of different materials, each layer dissolvable in different portions of digestive tract, the method comprising dissolving one of said layers in one portion of the digestive tract and dissolving another said layer in a different portion of the digestive tract.

3. The sampling method of claim 1 wherein the capsule (2) includes a filter, the method comprising filtering the sample of the body substance as it flows into the capsule.

4. The method of claim 1 further comprising piercing the capsule with an evacuation needle and removing from the capsule at least a part of the body fluid therewithin.

5. A sampling method for obtaining samples of internal body substances in a digestive tract of a patient, wherein an elongated capsule (2) having rounded end-portions is swallowed by the patient and the capsule (2) is opened in a predetermined position of the digestive tract following contact with a body substance to be collected, the method comprising:

a) opening an inlet opening (18) provided in an end-portion of the capsule (2) and having the inlet opening extending in a direction along a longitudinal axis of the elongated capsule to initiate collection of a sample of the body substance by dissolving a plug member (20) within the inlet opening (18) in the capsule wall (3) following contact with the body substance to be collected;

b) opening a flexible, self-sealing blocking member (12), disposed within an inner chamber defined by capsule walls comprised of a permanently joined cap and body member, by flexible movement of the blocking member (12) in the direction along the longitudinal axis of the elongated capsule to collect the sample of the body fluid by the force of vacuum or substantial under-pressure in the capsule (2) when the plug member (20) has been dissolved, wherein said blocking member (12) is adjacent to and spaced from the inlet opening (18) and has at least one laterally located aperture for a through-flow of the body fluid into the inner chamber; and c) blocking the inlet opening (18) with the flexible blocking member (12) by flexible movement of the flexible blocking member in the direction along the longitudinal axis of the elongated capsule, caused by internal resilience of the blocking member from the inside of the capsule (2) when the vacuum or substantial under-pressure in the capsule has been equalised.

\* \* \* \* \*